United States Patent [19]

Harnisch et al.

[11] Patent Number: 4,841,052

[45] Date of Patent: Jun. 20, 1989

[54] NAPHTHALIC ACID IMIDES ELECTROPHOTOGRAPHIC TONERS

[75] Inventors: Horst Harnisch, Much; Roderich Raue, Leverkusen, both of Fed. Rep. of Germany

[73] Assignee: Bayer Aktiengesellschaft, Leverkusen, Fed. Rep. of Germany

[21] Appl. No.: 225,329

[22] Filed: Jul. 28, 1988

Related U.S. Application Data

[62] Division of Ser. No. 10,364, Feb. 3, 1987.

[30] Foreign Application Priority Data

Feb. 15, 1986 [DE] Fed. Rep. of Germany ....... 3604827

[51] Int. Cl.$^4$ .......... C07D 471/06

[52] U.S. Cl. .......... 544/361; 546/99

[58] Field of Search .......... 544/361; 546/99

[56] References Cited

U.S. PATENT DOCUMENTS

| | | | |
|---|---|---|---|
| 3,880,859 | 4/1975 | Scheuermann et al. | 544/361 |
| 3,898,234 | 8/1975 | Burdeska | 544/361 |
| 3,940,398 | 2/1976 | Wade et al. | 544/361 |
| 3,953,451 | 4/1976 | Hell et al. | 544/361 |
| 4,007,191 | 2/1977 | Wade et al. | 546/99 |
| 4,077,958 | 3/1978 | Wade et al. | 546/99 |
| 4,139,532 | 2/1979 | Scheuermann et al. | 544/361 |
| 4,204,063 | 5/1980 | Brana et al. | 546/99 |
| 4,220,777 | 9/1980 | Kay et al. | 546/99 |
| 4,499,266 | 2/1985 | Cheng et al. | 546/99 |
| 4,508,900 | 4/1985 | Schonbeyer et al. | 546/99 |
| 4,614,820 | 9/1986 | Zee-Cheng et al. | 546/99 |
| 4,665,071 | 5/1987 | Zee-Cheng et al. | 546/99 |
| 4,782,064 | 11/1988 | Wright et al. | 546/99 |

OTHER PUBLICATIONS

Harnisch, CA 107-79486x (1987) "Cationic Naphthalimide Fluorescence Quenchers".

*Primary Examiner*—Donald G. Daus
*Assistant Examiner*—Cecilia Shen
*Attorney, Agent, or Firm*—Sprung Horn Kramer & Woods

[57] ABSTRACT

Positively charged electrophotographic toners contain, in addition to conventional resin and pigment particles, an additive reinforcing the cationic charge, of the general formula

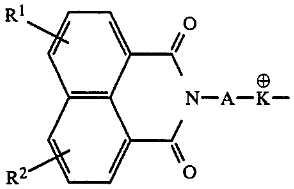

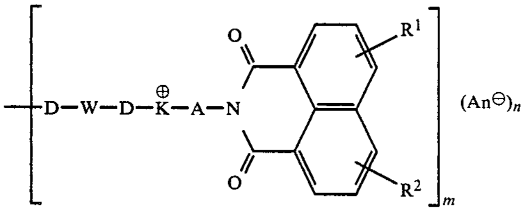

in which
$R^1$ and $R^2$ each represent hydrogen, chlorine, bromine, hydroxyl, $C_1$-$C_4$-alkoxy or carboxyl,
A represents $C_1$-$C_5$-alkylene or —$C_6H_4$—$CH_2$— (m or p),
m represents 0 or 1,
n represents 1 or 2
$K^\oplus$ represents

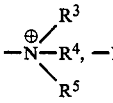 , 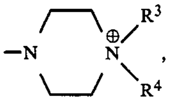 , or 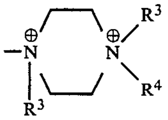

$R^3$ represents $C_1$-$C_{18}$-alkyl, carbamoyl-$C_1$-$C_2$-alkyl, $C_1$-$C_4$-alkoxycarbonyl-$C_1$-$C_2$-alkyl, benzyl, cyclohexyl or allyl,
$R^4$ represents $C_1$-$C_4$-alkyl or a single bond linked to D,
$R^5$ represents $C_1$-$C_4$-alkyl,
D represents —$CH_2$, —$CH_2$—CO—, —$CH_2$—CO—NH— or
W represents

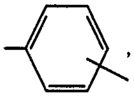

, 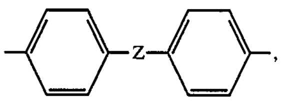 ,

—CO—
or a single bond,
Z represents —$CH_2$—,

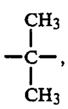

, 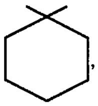 ,

—O—, —S—, —$SO_2$—
or a single bond and $An^\ominus$ represents an anion.

1 Claim, No Drawings

NAPHTHALIC ACID IMIDES ELECTROPHOTOGRAPHIC TONERS

This is a division of aplication Ser. No. 010,364, filed Feb. 3, 1987 now pending.

The invention relates to positively charged electrophotographic toners which contain, in addition to conventional resin and pigment particles, an additive reinforcing the cationic charge, of the general formula

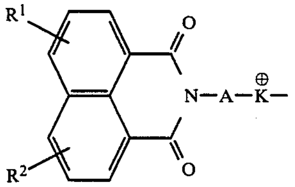

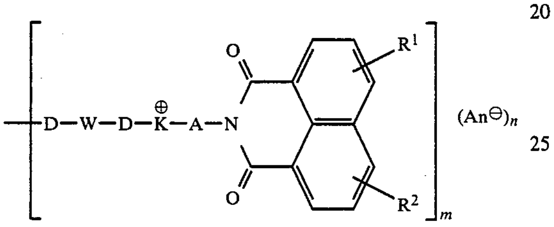

in which $R^1$ and $R^2$ each represent hydrogen, chlorine, bromine, hydroxyl, $C_1$–$C_4$-alkoxy carboxyl, A represents $C_1$–$C_5$-alkylene or —$C_6H_4$—$CH_2$— (m o r p ), m represents 0 or 1 n represents 1 or 2

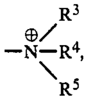, 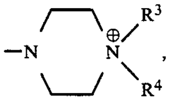, or 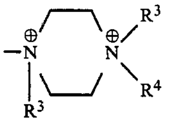

$R^3$ represents $C_1$–$C_{18}$-alkyl, carbamoyl -$C_1$–$C_2$-alkyl, $C_1$–$C_4$-alkoxycarbonyl-$C_1$-$C_2$-alkyl, benzyl, cyclohexyl or allyl, $R^4$ represents $C_1$–$C_4$-alkyl or a single bond linked to D, $R^5$ represents $C_1$–$C_4$-alkyl, D represents —$CH_2$—, —$CH_2$—CO—, —$CH_2$—CO—NH—or —$Ch_2$—CO—NH—$CH_2$—

W represents

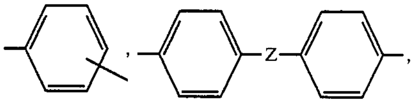

or a single bond,

Z represents

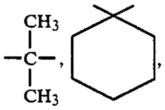

—S—, —$SO_2$— or a single bond and

An (—) represents an anion, to the use of the compounds (I) in electrographic toners and to novel naphtahlic acid imide derivatives.

$R^1$ and $R^2$ preferably denote hydrogen.

$C_1$–$C_5$-alkylene radicals A can be straight-chain or branched. $C_2$–$C_5$-alkylene radicals and in particular the n-propylene radical are preferred.

Preferred alkyl radicals $R^3$ are $C_1$–$C_{16}$-alkyl radicals.

Suitable anions are conventional anions such as halides, for example chloride, bromide and iodide, tetrafluoborates and aniouns of alkylsulphonic and arylsulphonic acids, of alkylcarboxylic and arylcarboxylic acids, of alkylphosphoric and arylphophoric acids and of alkylphosphonic and arylphosphonic acid. Anions which reduce the water-solubility of the compounds (I) and at the same time increase their solubility in organic solvents such as dimethylformamide, acetone, chloroform or toluene are particularly suitable. The reduction of water-solubility can however also be achieved by increasing the size of the alkyl radical $R^3$, i.e. by selecting it approximately in the range of $C_5$–$C_{16}$-alkyl. In this case more hydrophilic anions such as halides are also highly suitable.

The preferred water-solubility of the compounds (I) at 20° C. is below 3% by weight, in particular below 1% by weight. In addition to halides and tetrafluoborates, particularly preferred anions are arylsulphonates such as benzenesulphonates, optionally substituted by $C_1$–$C_{12}$-alkyl or chlorine, $C_5$–$C_{18}$-alkylsulphonates, salts of $C_5$–$C_{18}$-alkylcarboxylic acids and salts of condensation products of formaldehyde and arylsulphonic acids and/or optionally sulphonated 4,4'-dihydroxdiphenyl-sulphone.

Preferred compounds of the formula (I) correspond to the formula

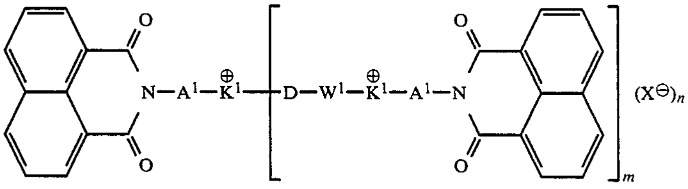 (II)

in which $A^1$ represents $C_2$–$C_5$-alkylene,

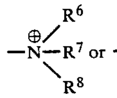 or 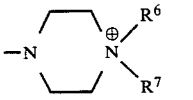

$R^6$ represents $C_1$–$C_{16}$-alkyl, carbamoylmethyl or benzyl, $R^7$ represents methyl or ethyl or a single bond linked to D, $R^8$ represents methyl or ethyl, $W^1$ represents

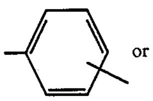 or 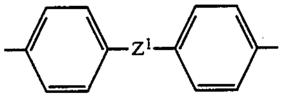

$Z^1$ represents —$CH_2$—,

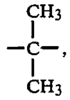,

L—O— or —$SO_2$— and $X^\ominus$ represents an anion, and

D, m and n have the same meaning as in formula (I).

The compounds of the formula (I) can be prepared by known methods, for example by the method described in DE-A No. 3,535,496. The compounds themselves are mostly known.

Charge-reinforcing additives for electrophotographic toners, also referred to as charge-regulating substances, are already known. They are described, for example in U.S. Pats. Nos. 3,893,935, 3,944,493, 4,007,293, 4,079,014, 4,298,672, 4338,390, 4,394,430 and 4,493,883.

Latent electrostatic image recordings are developed by inductive deposition of the toner on the electrostatic image. The charge-regulating substances reinforce the cationic charge of the toner. The image thereby becomes stronger and sharper.

Such charge-regulating substances must meet a variety of requirements. 1. Capability of developing the latent electrostatic image to a strongly coloured visible image. 2. Ready dispersibility in the toner composition and uniform dispersion on the image surface in order to produce a defect-free, sharp, homogeneous image. 3. Insensitivity to moisture. 4. High thermal stability. 5. Resistance to the hot mixture of lead oxide and a vinylidene fluoride/hexafluoropropylene copolymer resin (for example VITION® E-430 from Dupont) which can be used to fix the image with the aid of a hot roller. The coating composition must not turn black as a result of decomposition products. 6. Absence of toxicity.

The charge-regulating substances known from the abovementioned U.S. patents by no means meet all these requirements.

It has now been found, surprisingly, that the substances (I) are highly suitable as charge-regulating substances in toners. In comparison with the cationic phtahalimide compounds known from U.S. Pat. No. 4,493,883, the compounds (I) produce a distinct increase in the colour strength of the developed image and an improvement in image sharpness. A further advantage is the considerably improved pH stability, which allows the preparation both of the compounds and of the toner compositions without any problems.

The resins contained in the toners are known. they are thermoplastic and have a softening point between 50° and 130° C., preferably between 65° C. Examples of such resins are polystyrene, copolymers of styrene with an acrylate or methacrylate, copolymers of styrene with butadiene and/or acrylonitrile, polyacrylates ad polymethacrylates, copolymers of an acrylate or methacrylate with vinyl chloride or vinyl acetate, polyvinyl chloride, copolymers of vinyl chloride with vinylidene chloride, copolymers of vinyl chloride with vinyl acetate, polyester resins (U.S. Pat. No. 3,590,000), epoxy resins, polyamides and polyurethanes.

In addition to the compounds (I) and the thermoplastic resins, the toners according to the invention contain known amounts of colouring materials and magnetically attractable material. The colouring material can consist of an organic dyestuff such as nigrosin, aniline blue, 2,9-dimethylquinacridone, C.I. Disperse Red 15 (=C.I. 60,710), C.I. Solvent Red 19 (=C.I. 26,050), C.I. pigment Blue 15 (=C.I. 74,160), C.I. Pigment Blue 22 (=C.I. 69,810) and C.I. Solvent Yellow 16 (=C.I. 12.700), or an inorganic pigment such as carbon black, red lead, yellow lead oxide or chrome yellow. Generally, the amount of the colouring material present in the toners does not exceed about 15% by weight.

The magnetically attractable material can consist of, for example, iron, nicklel, chromium oxide, iron oxide or a fereite of the general formula $MFe_2O_4$, in which M represents a divalent metal such as iron, cobalt, zinc, nickel or manganese.

The preparation of the toners containing the compounds (I) is carried out by conventional methods, for example by melting the thermoplastic resin or a mixture of the thermoplastic resins, then finely dispersing one or more charge-regulating substances of the formula (I) and other additives, if used, in the molten resin, using the mixing and kneading machinery known for this purpose, then cooling the melt to a solid mass and finally grinding the solid mass to particles of the desired particle size. It is also possible to dissolve the thermoplastic resin and the copound (I) in a common solvent, incorporate the other additives into the solution and then spray-dry the liquid in a manner known per se or evaporate the solvent or solvents and grind the solid residue to particles of the desired particle size. In a modification of this method of preparation, the carge-regulating substance of the formula (I) is not dissolved but finely despersed in the solution of the thermoplastic resin.

The toner compositionobtained in this manner is then used, for exmple by analogy with U.S. Pat. No. 4,265,990, in a xereographic image-recording system. The photoreceptors employed for this purpose must be capable of becoming negatively charge. Examples are those likewise described in U.S. Pat. No. 4,265,990. They can contain, for example, the substances listed below in the chargegenerating layer: 4-dimethylaminobenzylidenebenzhydrazide, polybinylcarbazole, 2-benzylideneaminocarbazole, 2-nitrobenzylidene-p-bromoaniline, 2,4-diphenylquinazoline, 1,5-diphenyl-3-methylpyrazoline, 1,3,5,-triphenylpyrazoline, charge-transfer complex from polyvinylcarbazole and trinitrofluorenone, 2-(4'-dimethylaminophenyl)-benzoxazole, selenium, tellurium, and arsenic triselenide.

The photoreceptors used can also additionally contain sensitizing dyes in the charge-generating layer, such as, for example, Bengal pink or eosine G. The photoreceptors can contain diamines in the charge-transporting layer, as are likewise mentioned in U.S. Pat. No. 4,265,990.

The compounds of the formula (II) are also a subject or the invention.

EXAMPLE 1

282 g of naphthalic acid N-3-dimethylaminopropy)-imide (1 mole) and 175.5 g of 4,4'-bis-(choroacetamidophenyl)-methane (0.5 mole) are heated in 1330 g of polyglycol (mean molecular weight 400) at 100° C. for 3 hours, a clear viscous sölution initially forming from which a colourless crystalline precipitate subsquently separates. After cooling to room temperature, the reaction mixture is diluted with 3.3 l or isopropanol with stirring, the crystalline precipitate is filtered off with suction, washed with isopropanol until the washing are colourless and dried in vacuo at 60° C. 444 g (97% of theory) of a compound of the formula

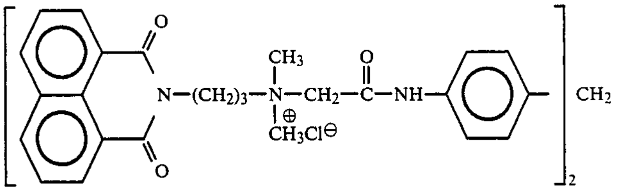
1 are obtained. The substance is virtually pure, as shown by thin-layer chromatography. 1 exhibits flourescence quenching on the fluoresent silica gel plate. Rf: 0.3 (mobile phase: 45% by volume of butyl acetate, 33% by volume of glacial acetic acid, 9% by volume of formic acid and 13% by volume of water).

The compound listed below are prepared in an analogous manner:

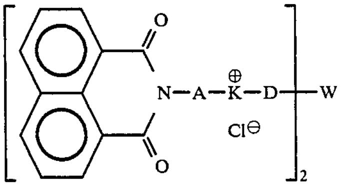

| Example | A | ⊕ —K— | D | W |
|---|---|---|---|---|
| 2 | 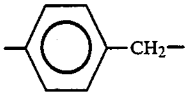 | 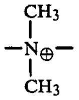 | $-CH_2-CO-NH$ | 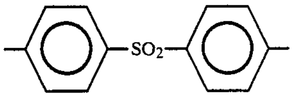 |
| 3 | 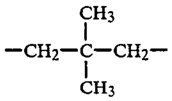 | 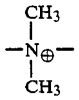 | $-CH_2-CO-NH-$ | 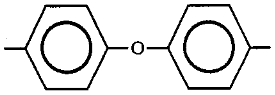 |
| 4 | $-CH_2-CH_2-$ | 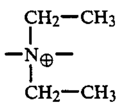 | $-CH_2-CO-NH$ | 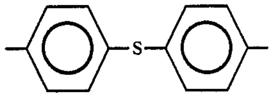 |
| 5 | $-CH_2-CH_2-CH_2-$ | 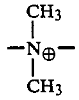 | $-CH_2-CO-NH-$ | 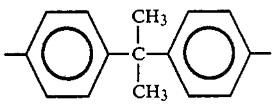 |
| 6 | 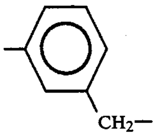 | 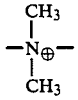 | $-CH_2-CO-NH-CH_2-$ | 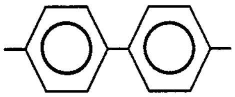 |
| 7 | $-CH_2-CH_2-$ | 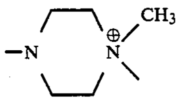 | $-CH_2-$ | $-CO-$ |
| 8 | 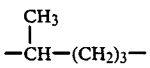 | 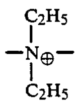 | $-CH_2-$ | 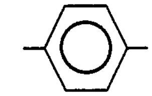 |

-continued

| Example | A | $\overset{\oplus}{-K-}$ | D | W |
| --- | --- | --- | --- | --- |
| 9 | $-CH_2-CH_2-$ | 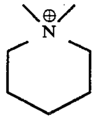 | $-CH_2-CO-$ | 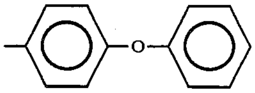 |
| 10 | 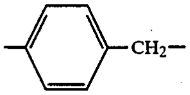 | 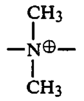 | $-CH_2-CO-NH-$ | 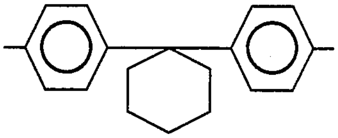 |

The compounds listed below are also prepared in an analogous manner:

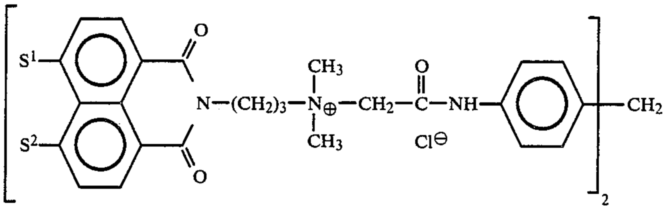

| Example | $S^1$ | $S^2$ |
| --- | --- | --- |
| 11 | Cl | H |
| 12 | Cl | Cl |
| 13 | $CH_3-O-$ | H |
| 14 | $C_2H_5-O-$ | H |
| 15 | $CH_3-O-$ | $CH_3-O-$ |
| 16 | $C_2H_5O-$ | $C_2H_5-O-$ |
| 17 | Br | H |
| 18 | Br | Br |
| 19 | COOH | H |
| 20 | COOH | COOH |

EXAMPLE 21

282 g of naphthalic acid N-(3-dimethylaminopropyl)-imide are reacted with 1755 g of 4,4'-bis-(chloroacetamidophenyl)-methane in 1330 g of polyglycol at 100° C. for 3 hours in the same manner as described in Example 1, 600 ml of ethanol and 225 g of p-toluenesulphonic acid are added, the mixture is heated to boiling under reflux for 2 hours, and the colourless crystalline precipitate is filtered off with suction, washed with 800 ml of ethanol and dried in vacuo at 60° C.

366 g of a compound of the formula

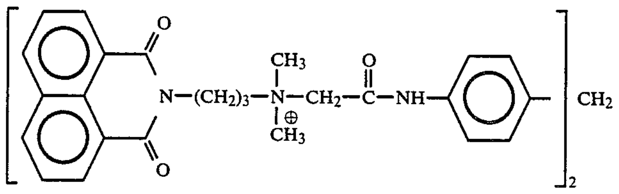

21

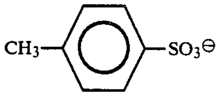

Melting Point 186–188° C.

are obtained, melting point 186°–188° C. The substance is virtually pure, as shown by thin-layer chromatography.

The p-toluenesulphonates and benzenesulphonates of the compounds 2 to 20 are also prepared in an analogous manner.

EXAMPLE 22

56.5 g (0.2 mole) of naphthalic acid N-(3-dimethylaminopropyl)-imide are suspended in 700 ml of toluene; 56 g of methyl p-toluenesulphonate are added with stirring, and stirring is continued at 60° C. for 1 hour. The colourless crystalline precipitate is filtered off with suction, washed with 150 ml of isopropanol and dried in vacuo at 40° C. 87 g (93% of theory) of a compound of the formula

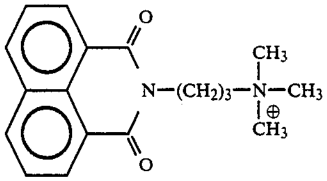

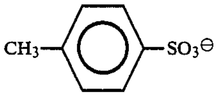

22 are obtained. The substance is entirely pure, as shown by thin-layer chromatography. It melts at 220°-221° C.

The substances listed below of the formula

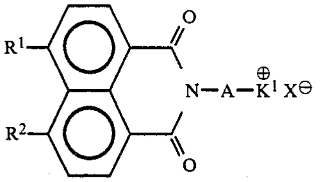

are prepared in an analogous manner.

| Example | $R^1$ | $R^2$ | A | $K^{1\oplus}$ | $X^{\ominus}$ |
|---|---|---|---|---|---|
| 23 | H | H | 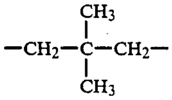 | 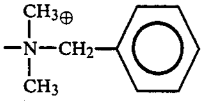 | $Cl^{\ominus}$ |
| 24 | H | H | $-CH_2-CH_2-$ | 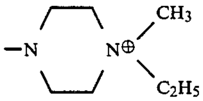 | $C_2H_5OSO_3^{\ominus}$ |
| 25 | H | H | 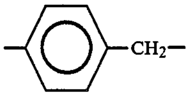 | 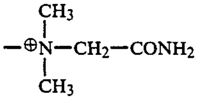 | $Cl^{\ominus}$ |
| 26 | H | H | 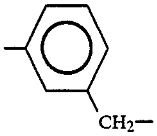 | 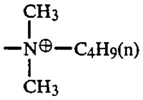 | $BF_4^{\ominus}$ |
| 27 | Cl | H | $-(CH_2)_2-$ | 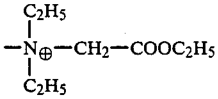 | 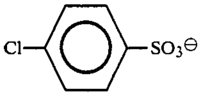 |
| 28 | Cl | Cl | $-(CH_2)_3-$ | 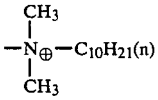 | $O^{\ominus}$ |
| 29 | Br | H | $-(CH_2)_2-$ | 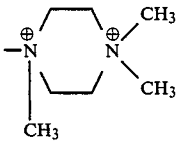 | $2CH_3OSO_3^{\ominus}$ |
| 30 | $CH_3O$ | H | $-(CH_2)_3-$ | 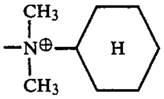 | $Br^{\ominus}$ |
| 31 | $C_2H_5O$ | $C_2H_5O$ | 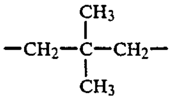 | 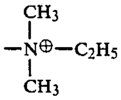 | 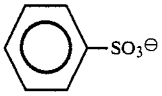 |

-continued

| Example | $R^1$ | $R^2$ | A | $K^{1\oplus}$ | $X^\ominus$ |
|---|---|---|---|---|---|
| 32 | COOH | H | $-(CH_2)_3-$ | 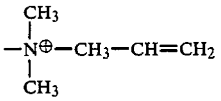 | $Br^\ominus$ |
| 33 | H | H | $-(CH_2)_3-$ | 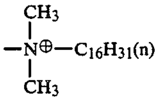 | $Cl^\ominus$ |

EXAMPLE 34

282 g (1 mole) of naphthalic acid N-(3-dimethylaminopropyl)-imide are suspended in 2 l of acetonitrile, and the suspension is treated with 307 g (1 mole) of 1-bromohexadecane with stirring and heated to boiling under reflux for 15 hours. The solution is filtered warm at 35° C. to remove small amounts of undissolved components. The filtrate is stirred with 2.5 l of acetone and cooled to −5° C. The crystalline precipitate is filtered off with suction, washed first with acetone then with petroleum ether, and dried in vacuo at 30° C. 540 g (92% of theroy) of a compound of the formula (34)

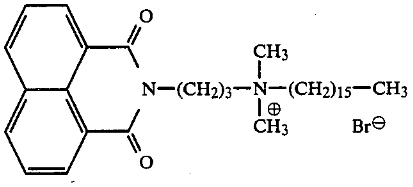

are obtained.

EXAMPLE 35

289 g (1.02 mole) of naphthalic acid N-(3-dimethylaminopropyl)-imide are suspended in 6.1 l of toluene and the suspension is treated dropwise with 138 g (1.09 mole) of dimethyl sulphate at 60° to 65° C. with stirring, and stirring is continued at 60° to 65° C. for 6 hours. After cooling to room temperature, the crystalline precipitate is filtered off with suction, washed with toluene and dried in vacuo at 50° C. 408 g (98% of theory) of a compound of the formula (35A)

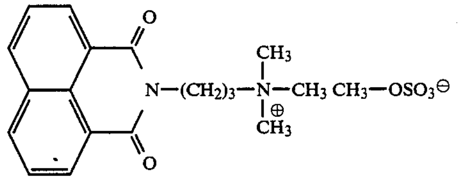

are obtained.

408 g (1 mole) of the compound obtained (35 A) are dissolved in 4 l of water at room temperature and the solution is treated dropwise, with stirring, with 1 l of a 40% strength aqueous solution of a polycondensation productof sulphonated 4,4'-dihydroxydiphenylsulphone and formaldehyde. The crystalline precipitate is filtered off with suction, washed with water and dried in vacuo at 50° C. 685 g of a compound of the formula (35)

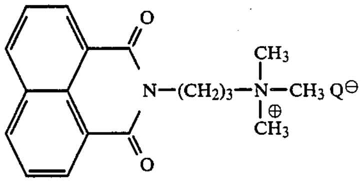

are obtained.

$Q^\ominus$ = equivalent of an anion obtained by condensing 4,4'-dihydrodiphenylsulphone, sulphuric acid and formaldehyde in the molar ratio 1:1:0.67.

Application example 2 per cent by weight of the compound from Example 22, 6 per cent by weight of carbon black and 92 per cent by weight of a styrene/butadiene resin containing 89 per cent by weight of styrene and 11 per cent by weight of butadiene are melted together in a ectruder at 100° C. and kneaded, and subsequently comminuted and ground until the particle diameter is smaller than 5 μ.

This toner composition is incorporated into a xerographic image recording system, such as that described in U.S.Pat. No. 4,265,990. For this purpose a MYLAR®substrate is provided with a polyvinylcarbazole layer which is chargegenerating when illuminated and in which trigonal selenium is freely dispersed; this is overlaid with a transparent charge-transporting layer containing N,N'-diphenyl-N,N'-bis-(3-methylphenyl)-1,1'-bisphenyl-4,4'-dimanine, dispersed in a MAKROLON®polycarbonate composition, as the charge-transporting molecule.

Microscopically sharp image recordings are obtained which in their sharpness are superior even to those produced according to U.S. Pat. No. 4,493,883, Example 1.

We claim:

1. A naphthalic acid imide of the formula

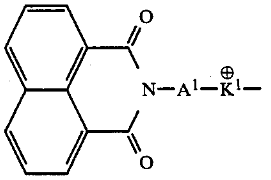

-continued

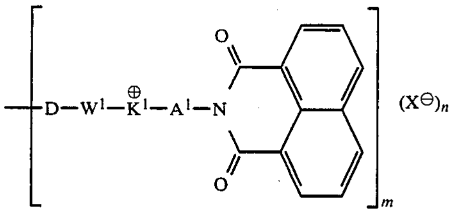

in which $A^1$ represents $C_2$–$C_5$-alkylene, $^{\oplus}K^1$ represents

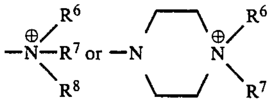

$R^6$ represents $C_1$–$C_{16}$-alkyl, carbamoylmethyl or benzyl, $R^7$ represents methyl or ethyl or a single bond linked to D, $R^8$ represents methyl or ethyl, $W^1$ represents

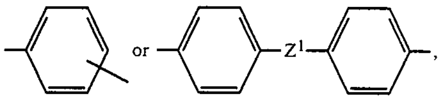

$Z^1$ represents —$CH_2$—,

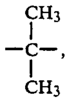

—O— or —$SO_2$— and $X^{\ominus}$ represents an unsubstituted benzosulphonate or a benzenesulphonate substituted by chlorinr or $C_1$–$C_{12}$-alkyl, a $C_5$–$C_{18}$-alkylsulphonate or a salt of a $C_5$–$C_{18}$-alkylcarboxylic acid or a salt of a condensation product of formaldehyde and arylsulphonic acids and/or optionally sulphonated 4,4'-dihydroxy-diphenylsulphone, wherein D represents —$CH_2$—, —$CH_2$—CO—, —$CH_2$—CO—NH—or —$CH_2$—CO—NH—$CH_2$— m represent 0 or 1 and

* * * * *

UNITED STATES PATENT AND TRADEMARK OFFICE
CERTIFICATE OF CORRECTION

PATENT NO. : 4,841,052

DATED : June 20, 1989

INVENTOR(S) : Horst Harnisch et al

It is certified that error appears in the above-identified patent and that said Letters Patent is hereby corrected as shown below:

| | |
|---|---|
| Col. 1, line 40 and Col. 3, line 5 | Before formula insert --K$^{\oplus}$ represents-- |
| Col. 1, line 52 | After "or" delete "-$Ch_2$" and substitute -- -$CH_2$-- |
| Col. 2, line 1 | After formula insert -- -CO- -- |
| Col. 2, line 13 | After formula insert -- -O-, -- |
| Col. 2, lines 19-20 | Correct spelling of --naphthalic-- |
| Col. 2, line 28 | Correct spelling of --anions-- |
| Col. 2, line 30 | Correct spelling of --arylphosphoric-- |
| Col. 3, line 27 | Before "-O-" delete "L" |
| Col. 3, line 54 | Delete "VITION" and substitute --VITON-- |
| Col. 3, line 64 | Correct spelling of --phthalimide-- |
| Col. 4, line 5 | After "65°C." insert --and 115°C.-- |
| Col. 4, line 8 | Delete "ad" and substitute --and-- |
| Col. 4, line 31 | Correct spelling of --ferrite-- |
| Col. 4, line 44 | Correct spelling of --compound-- |
| Col. 4, line 49 | Delete "carge-" and substitute --charge- -- |
| Col. 4, line 51 | Correct spelling of --dispersed-- |
| Col. 4, line 53 | Insert a space between "composition" and "obtained" |
| Col. 4, line 54 | Correct spelling of --example-- |
| Col. 4, line 55 | Correct spelling of --xerographic-- |
| Col. 4, line 61 | Correct spelling of --polyvinylcar- -- |
| Col. 5, line 18 | Delete "or" and substitute --of-- |
| Col. 5, line 21 | Correct --dimethylaminopropyl)- -- |
| Col. 5, line 22 | Correct --chloroacetamido- -- |
| Col. 5, line 26 | Correct spelling of --subsequently-- |

UNITED STATES PATENT AND TRADEMARK OFFICE
CERTIFICATE OF CORRECTION

PATENT NO. : 4,841,052      Page 2 of 3

DATED : June 20, 1989

INVENTOR(S) : Horst Harnisch et al

It is certified that error appears in the above-identified patent and that said Letters Patent is hereby corrected as shown below:

| | |
|---|---|
| Col. 6, line 15 | Correct spelling of --fluorescent-- |
| Col. 7, Example 10, third column | Delete formula and substitute -- 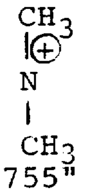 -- |
| Col. 7, line 44 | Delete "1755" and substitute --175.5-- |
| Col. 10, Example 26, Ex. 30, Ex. 31, Ex. 32 and Col. 11, Ex. 33 fifth column of each | Move "$\oplus$" to --$\underset{\oplus}{CH_3}$-- |
| Col. 10, Example 28, last column | Delete "O $\ominus$" and substitute --J $\ominus$-- |
| Col. 11, Example 32, fifth column | After "-N $\oplus$-" delete "$CH_3$" and substitute --$CH_2$-- |
| Col. 11, line 64 | Insert a space between "product" and "of" |
| Col. 12, line 40 | Correct spelling of --extruder-- |
| Col. 12, line 50 | Correct spelling of --diamine-- |
| Col. 14, line 17 | Correct spelling of --chlorine-- |

UNITED STATES PATENT AND TRADEMARK OFFICE

CERTIFICATE OF CORRECTION

PATENT NO. : 4,841,052

DATED : June 20, 1989

INVENTOR(S) : Horst Harnisch et al

It is certified that error appears in the above-identified patent and that said Letters Patent is hereby corrected as shown below:

Col. 14, line 26 Insert --n represents 1 or 2.--

Signed and Sealed this

Fourth Day of December, 1990

Attest:

HARRY F. MANBECK, JR.

Attesting Officer

Commissioner of Patents and Trademarks